United States Patent
Selby et al.

(10) Patent No.: US 9,473,749 B2
(45) Date of Patent: Oct. 18, 2016

(54) VISUAL INSPECTION DEVICE INCLUDING A MOVEABLE DISPLAY

(75) Inventors: David A. Selby, Oconomowoc, WI (US); Steven W. Hyma, Milwaukee, WI (US); Corey J. Dickert, Brookfield, WI (US); Scott Schneider, Waukesha, WI (US); Matthew J. Mergener, Germantwown, WI (US)

(73) Assignee: MILWAUKEE ELECTRIC TOOL CORPORATION, Brookfield, WI (US)

( * ) Notice: Subject to any disclaimer, the term of this patent is extended or adjusted under 35 U.S.C. 154(b) by 574 days.

(21) Appl. No.: 13/398,540

(22) Filed: Feb. 16, 2012

(65) Prior Publication Data

US 2012/0206591 A1 Aug. 16, 2012

Related U.S. Application Data

(60) Provisional application No. 61/443,467, filed on Feb. 16, 2011.

(51) Int. Cl.
| | |
|---|---|
| *H04N 7/18* | (2006.01) |
| *H04N 5/232* | (2006.01) |
| *A61B 1/00* | (2006.01) |
| *A61B 1/04* | (2006.01) |
| *G02B 23/24* | (2006.01) |
| *H04N 5/225* | (2006.01) |

(52) U.S. Cl.
CPC ........... *H04N 7/183* (2013.01); *A61B 1/00052* (2013.01); *A61B 1/00105* (2013.01); *A61B 1/042* (2013.01); *G02B 23/2484* (2013.01); *H04N 5/232* (2013.01); *H04N 2005/2255* (2013.01)

(58) Field of Classification Search
CPC ................. H04N 5/232; H04N 7/183; H04N 2005/2255; G02B 23/2484; A61B 1/00052; A61B 1/042; A61B 1/00105
See application file for complete search history.

(56) References Cited

U.S. PATENT DOCUMENTS

| | | |
|---|---|---|
| 5,928,137 A | 7/1999 | Green |
| 6,221,007 B1 | 4/2001 | Green |
| 6,248,017 B1 | 6/2001 | Roach |

(Continued)

FOREIGN PATENT DOCUMENTS

| | | |
|---|---|---|
| CN | 201497709 | 6/2010 |
| JP | 2011330784 | 11/2001 |

(Continued)

OTHER PUBLICATIONS

PCT/US2012/025465 International Search Report and Written Opinion dated Sep. 12, 2012, 10 pages.

(Continued)

*Primary Examiner* — Joseph Ustaris
*Assistant Examiner* — Jill Sechser
(74) *Attorney, Agent, or Firm* — Michael Best & Friedrich LLP

(57) ABSTRACT

A visual inspection device includes a housing with a support portion and a grip portion extending from the support portion, a flexible cable having a first end coupled to the housing and a second end, a camera assembly coupled to the second end of the flexible cable and operable to transmit image data through the flexible cable, and a display movably coupled to the support portion of the housing and operable to present an image derived from the image data.

16 Claims, 6 Drawing Sheets

(56) References Cited

U.S. PATENT DOCUMENTS

| | | | |
|---|---|---|---|
| 7,174,195 B2 | 2/2007 | Nagamine | |
| 7,214,183 B2 | 5/2007 | Miyake | |
| 7,369,882 B2 | 5/2008 | Hawang et al. | |
| 7,833,152 B2 | 11/2010 | Chatenever et al. | |
| 7,869,840 B2 | 1/2011 | Kim et al. | |
| 7,946,981 B1* | 5/2011 | Cubb | 600/194 |
| 8,189,043 B2* | 5/2012 | Schneider et al. | 348/82 |
| 8,659,652 B2* | 2/2014 | Schneider et al. | 348/82 |
| 2002/0022769 A1 | 2/2002 | Smith et al. | |
| 2003/0195390 A1 | 10/2003 | Graumann | |
| 2005/0001821 A1* | 1/2005 | Low | G06F 3/0362 345/169 |
| 2006/0167340 A1 | 7/2006 | Pease et al. | |
| 2007/0281749 A1* | 12/2007 | Suga | 455/566 |
| 2008/0051628 A1* | 2/2008 | Pecherer | A61B 1/267 600/112 |
| 2009/0225159 A1 | 9/2009 | Schneider et al. | |
| 2010/0125166 A1 | 5/2010 | Henzler | |
| 2010/0145146 A1* | 6/2010 | Melder | 600/112 |

FOREIGN PATENT DOCUMENTS

| | | |
|---|---|---|
| JP | 2008119464 | 5/2008 |
| WO | 9926414 | 5/1999 |

OTHER PUBLICATIONS

GB1314694.9 Examination Report dated Sep. 19, 2014 (3 pages).

* cited by examiner

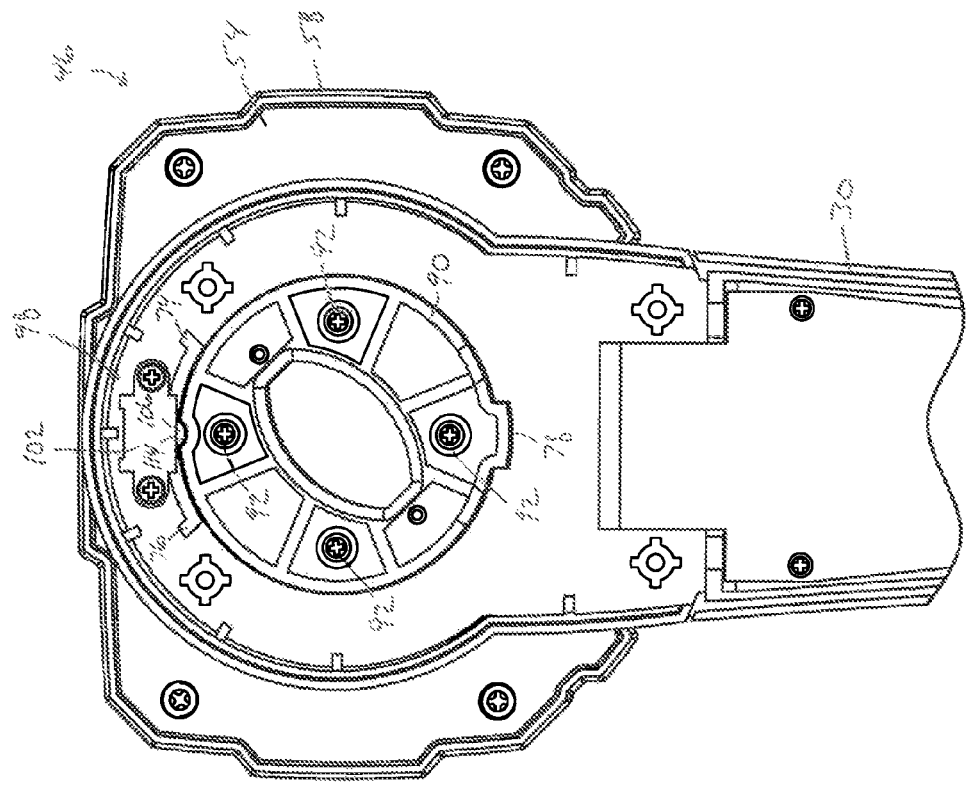

VISUAL INSPECTION DEVICE INCLUDING A MOVEABLE DISPLAY

CROSS-REFERENCE TO RELATED APPLICATIONS

This application claims priority to U.S. Provisional Patent Application No. 61/443,467 filed on Feb. 16, 2011, the entire contents of which is incorporated herein by reference.

FIELD OF THE INVENTION

The present invention relates to a visual inspection device and, more particularly, to a hand-held visual inspection device for viewing confined or otherwise difficult to access locations.

BACKGROUND OF THE INVENTION

Visual inspection devices (e.g., borescopes, endoscopes, or the like) provide tradespeople, such as plumbers, electricians, mechanics, HVAC (heating, ventilation, and air conditioning) professionals, welders, carpenters, MRO (maintenance, repair, and operations) professionals, or the like, with means to view locations that are inaccessible without dismantling or removing surrounding structures. For example, visual inspection devices are used to inspect inside pipes, walls, floors, aircraft or automobile engines, or other equipment that include narrow, small, and/or dark passageways. Some visual inspection devices have also been employed by surgeons to help view inside patients during, for example, surgery.

SUMMARY OF THE INVENTION

The invention provides, in one aspect, a visual inspection device including a housing with a support portion and a grip portion extending from the support portion, a flexible cable having a first end coupled to the housing and a second end, a camera assembly coupled to the second end of the flexible cable and operable to transmit image data through the flexible cable, and a display movably coupled to the support portion of the housing and operable to present an image derived from the image data.

Other features and aspects of the invention will become apparent by consideration of the following detailed description and accompanying drawings.

BRIEF DESCRIPTION OF THE DRAWINGS

FIG. 5 is a front view of the visual inspection device of FIG. 1, illustrating a display of the inspection device oriented in a home position.

FIG. 6 is an enlarged, rear cross-sectional view of the visual inspection device of FIG. 1, illustrating a detent assembly for maintaining the display oriented in the home position.

Before any embodiments of the invention are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting.

DETAILED DESCRIPTION

Figure 1:
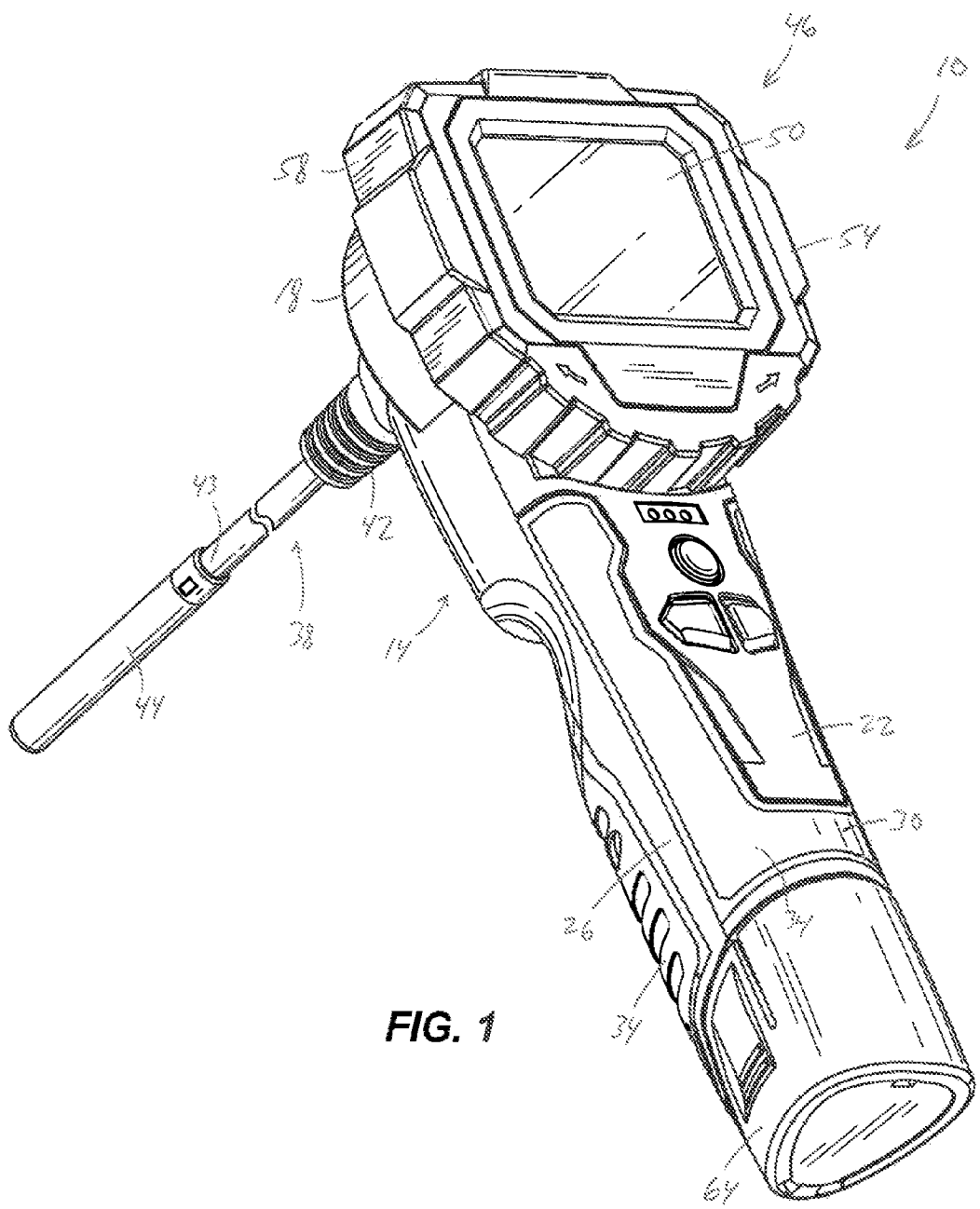
FIG. 1 is a front perspective view of a visual inspection device of the invention.
Figure 2:
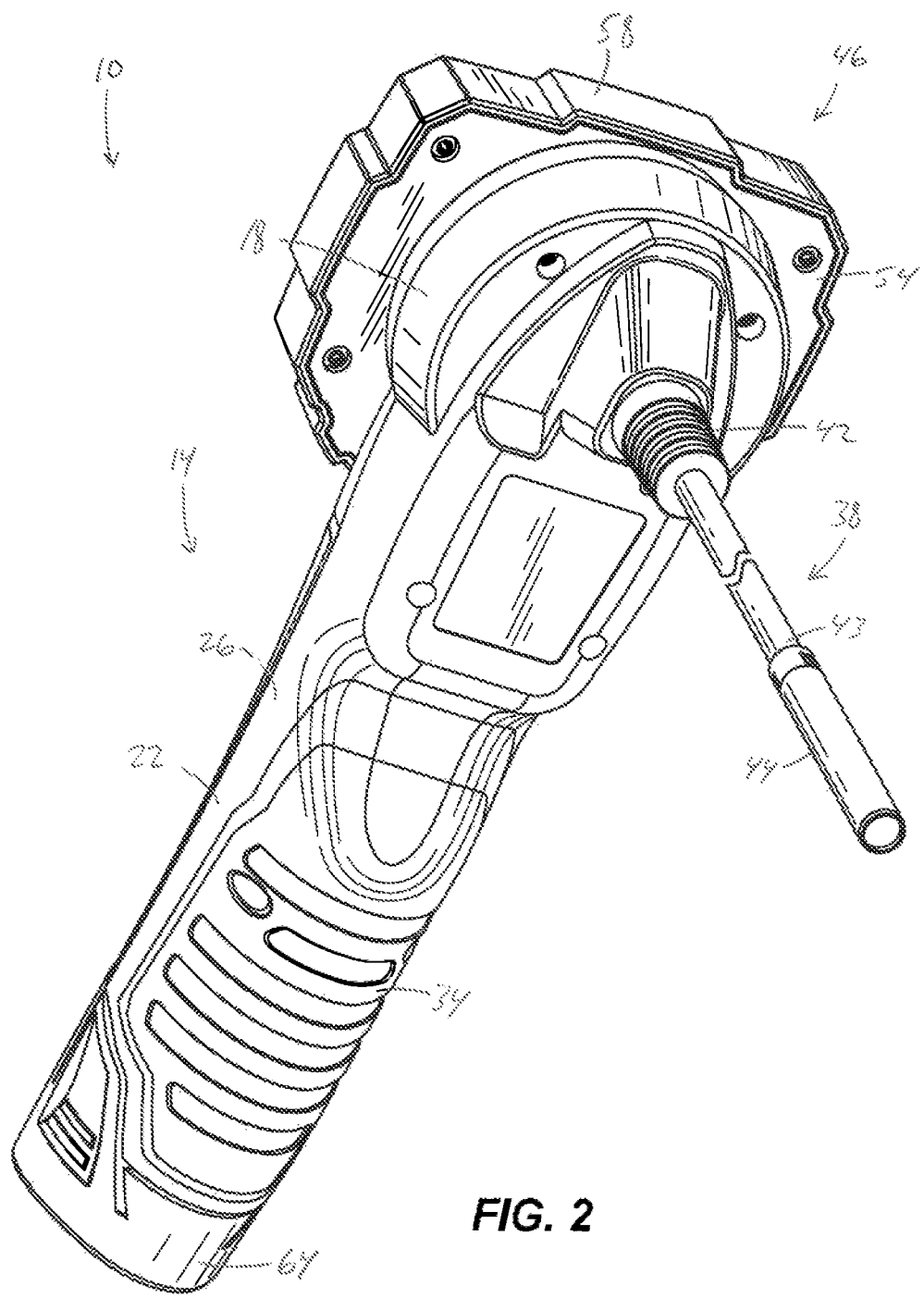
FIG. 2 is a rear perspective view of the visual inspection device of FIG. 1.

FIGS. 1 and 2 illustrate a visual inspection device 10 configured as a hand-held unit for a user (e.g., a plumber, an electrician, a mechanic, an HVAC professional, a welder, a carpenter, an MRO professional, or the like) to view the interior of a confined space (e.g., a pipe, a wall, a floor, an engine, or the like). The visual inspection device 10 includes a housing 14 having a support portion 18 and a grip portion 22 extending from the support portion 18. In the illustrated construction of the device 10, the housing 14 includes a first or a lower shell 26 and a second or an upper shell 30 coupled together in a clamshell manner (e.g., using fasteners, see FIG. 3). The grip portion 22 is defined by the lower and upper shells 26, 30, and is grasped by a user when maneuvering the device 10 during operation. An elastomeric overmold 34 is formed on each of the lower and upper shells 26, 30 to facilitate grasping the grip portion 22 and to help protect the housing 14 if the device 10 impacts a surface or is dropped.

Figure 3:
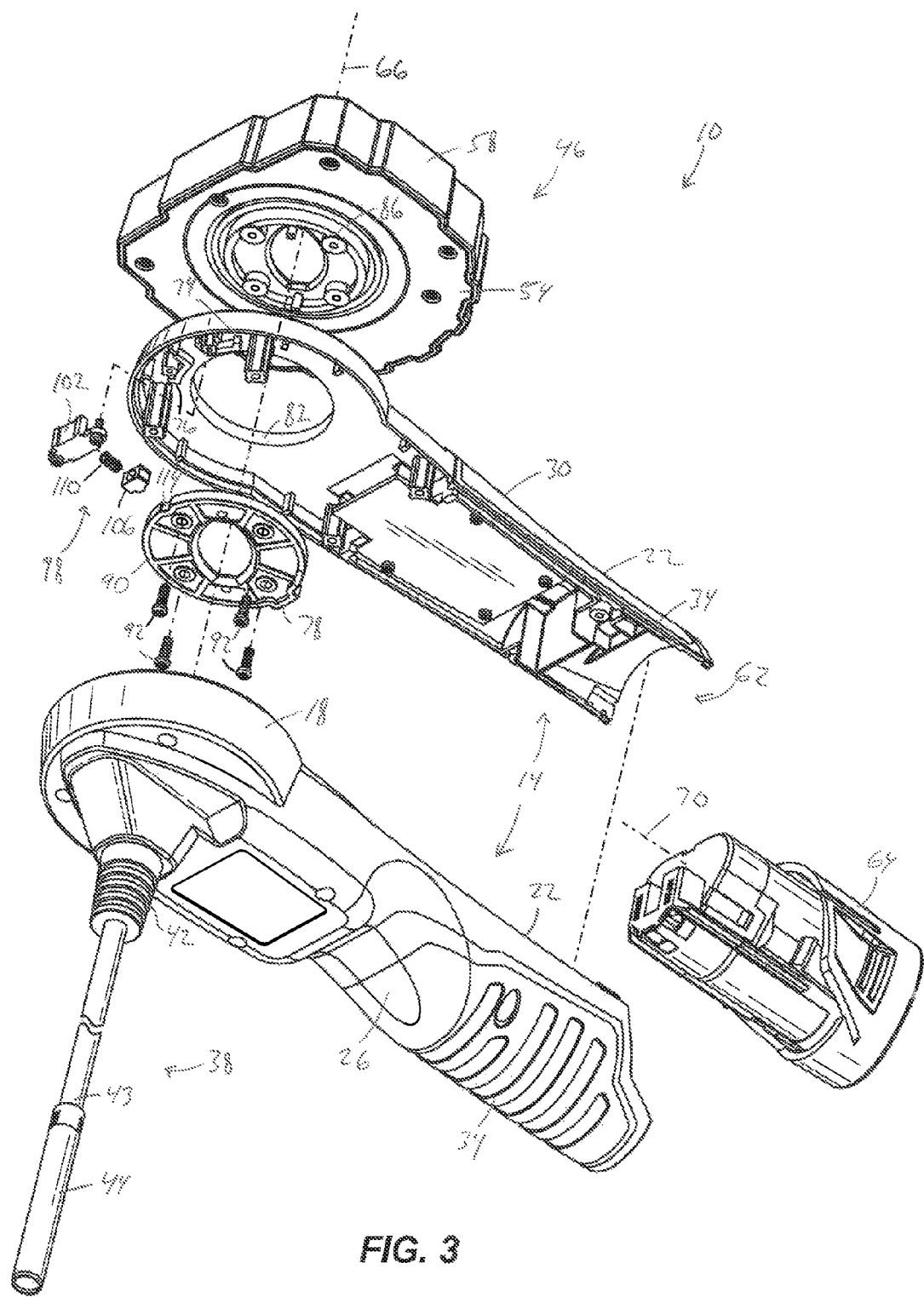
FIG. 3 is an exploded perspective view of the visual inspection device of FIG. 1.

With reference to FIGS. 1-3, the device 10 also includes a flexible cable 38 having a first end 42 coupled to the housing 10 and a second end 43 with a camera assembly 44 coupled thereto. In the illustrated construction of the device 10, the first end 42 of the flexible cable 38 is attached to the lower shell 26. Alternatively, the first end 42 of the flexible cable 38 may be attached to the housing 14 at any of a number of different locations. The camera assembly 44 is operable to transmit image data through the flexible cable 38. The camera assembly 44 and the flexible cable 38 may be similar to those disclosed in published U.S. Patent Application No. 2009/0225159, the entire contents of which is incorporated by reference herein.

The device 10 further includes a display 46 movably coupled to the support portion 18 of the housing 14. The display 46 includes a screen 50 and a bezel 54 surrounding the screen 50 (FIG. 1). The bezel 54 includes an overmold 58 to facilitate grasping the display 46 and to help protect the display 46 if the device 10 impacts a surface or is dropped. The display 46 is operable to present an image derived from the image data acquired from the camera assembly 44 and transmitted through the flexible cable 38. Other components and features of the display 46, particularly related to the screen 50 and the operation thereof, are described in published U.S. Patent Application No. 2009/0225159.

With reference to FIG. 3, the visual inspection device 10 includes a cavity 62 in the grip portion 22 of the housing 14 in which a battery pack 64 is removably received. Such a battery pack 64 may be configured as a rechargeable power tool battery pack 64 that is usable with a variety of power tools (e.g., drills, screwdrivers, saws, or the like). The battery pack 64 may be a twelve-volt (12V) battery pack 64. The battery pack 64 may also include three battery cells having, for example, a lithium (Li), lithium-ion (Li-ion), or other lithium-based chemistry. For example, the battery cells may have a chemistry of lithium-cobalt (Li—Co), lithium-manganese (Li—Mn) spinel, or Li—Mn nickel. In such embodiments, each battery cell may have a nominal voltage of about, for example, 3.6V, 4.0V, or 4.2V. In other embodiments, the battery cells may have a nickel-cadmium, nickel-metal hydride, or lead acid battery chemistry. In further embodiments, the battery pack 64 may include fewer or more battery cells, and/or each battery cell may have a different nominal voltage.

Figure 7:
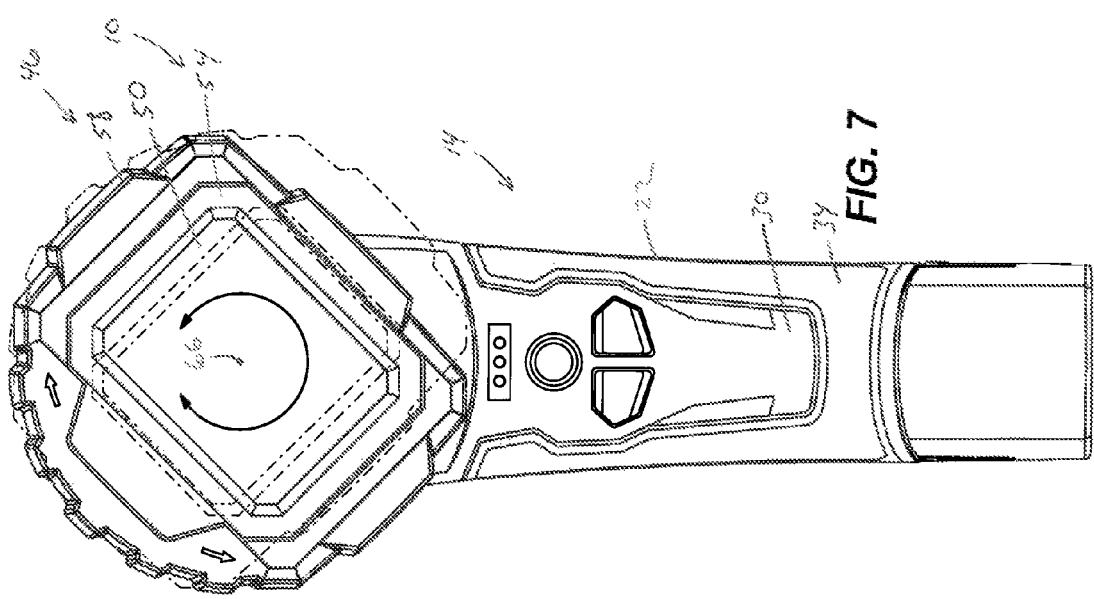
FIG. 7 is a front view of the visual inspection device of FIG. 1, illustrating the display rotated between first and second angular positions.

With reference to FIG. 7, the display 46 is pivotably or rotatably coupled to the support portion 18 of the housing 14. In the illustrated construction of the device 10, the display 46 is pivotable or rotatable about an axis 66 that is substantially aligned with the first end 42 of the flexible cable 38 (FIG. 3). The axis 66, in turn, is oriented substantially normal to a longitudinal axis 70 of the grip portion 22 of the housing 14. As such, the user of the device 10 may pivot or rotate the display 46 such that the image on the screen 50 coincides with the orientation with the user's head, irrespective of the angular orientation of the grip portion 22 of the housing 14 relative to the ground. Alternatively, the display 46 may be pivotable or rotatable about an axis that is offset from the first end 42 of the flexible cable 38. As a further alternative, the display 46 may be movably coupled to the housing 14 in another manner to otherwise permit the user to re-orient the display 46 relative to the housing 14.

With reference to FIG. 3, the housing 14 includes angularly spaced protrusions 74, 76 with respect to the rotational axis 66 of the display 46, and the display 46 includes a another protrusion 78 that is selectively engageable with either of the protrusions 74, 76 to limit the extent to which the display 46 may rotate relative to the housing 14. The protrusions 74, 76 are integrally formed as a single piece with the upper shell 30 of the housing 14. The protrusions 74, 76 are also positioned proximate an opening 82 in the upper shell 30 through which a cylindrical wall 86 on the display 46 is received to align the display 46 with the housing 14. As such, the cylindrical wall 86 pilots the display 46 on the housing 14 and maintains alignment of the display 46 with the rotational axis 66.

With continued reference to FIG. 3, the device 10 includes a plate 90 coupled to the display 46 (e.g., using fasteners 92) for co-rotation with the display 46. At least a portion of the upper shell 30 (e.g., the portion proximate the opening 82) is clamped between the plate 90 and the display 46 to secure the display 46 to the upper shell 30 of the housing 14. The protrusion 78 is configured as a radially outwardly extending tab on the plate 90.

Figure 8:
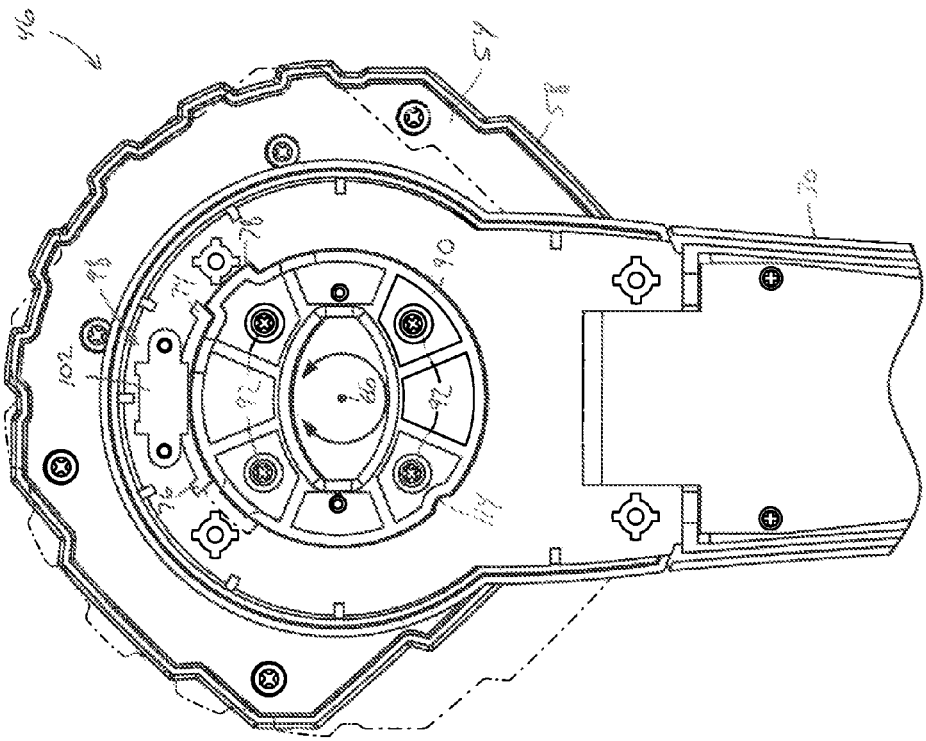
FIG. 8 is an enlarged, rear cross-sectional view of the visual inspection device of FIG. 1, illustrating respective protrusions on a housing of the inspection device and the display for limiting rotation of the display between the first and second angular positions.

With reference to FIG. 8, the respective protrusions 74, 78 are engageable to define a first angular position of the display 46 relative to the housing 14 (shown in solid lines), while the respective protrusions 76, 78 are engageable to define a second angular position of the display 46 relative to the housing 14 (shown in phantom or dashed lines). In the illustrated construction of the device 10, the display 46 is rotatable about 270 degrees between the first and second angular positions of the display 46 relative to the housing 14. Alternatively, the display 46 may be configured to rotate more or less than about 270 degrees relative to the housing 14.

Figure 4:
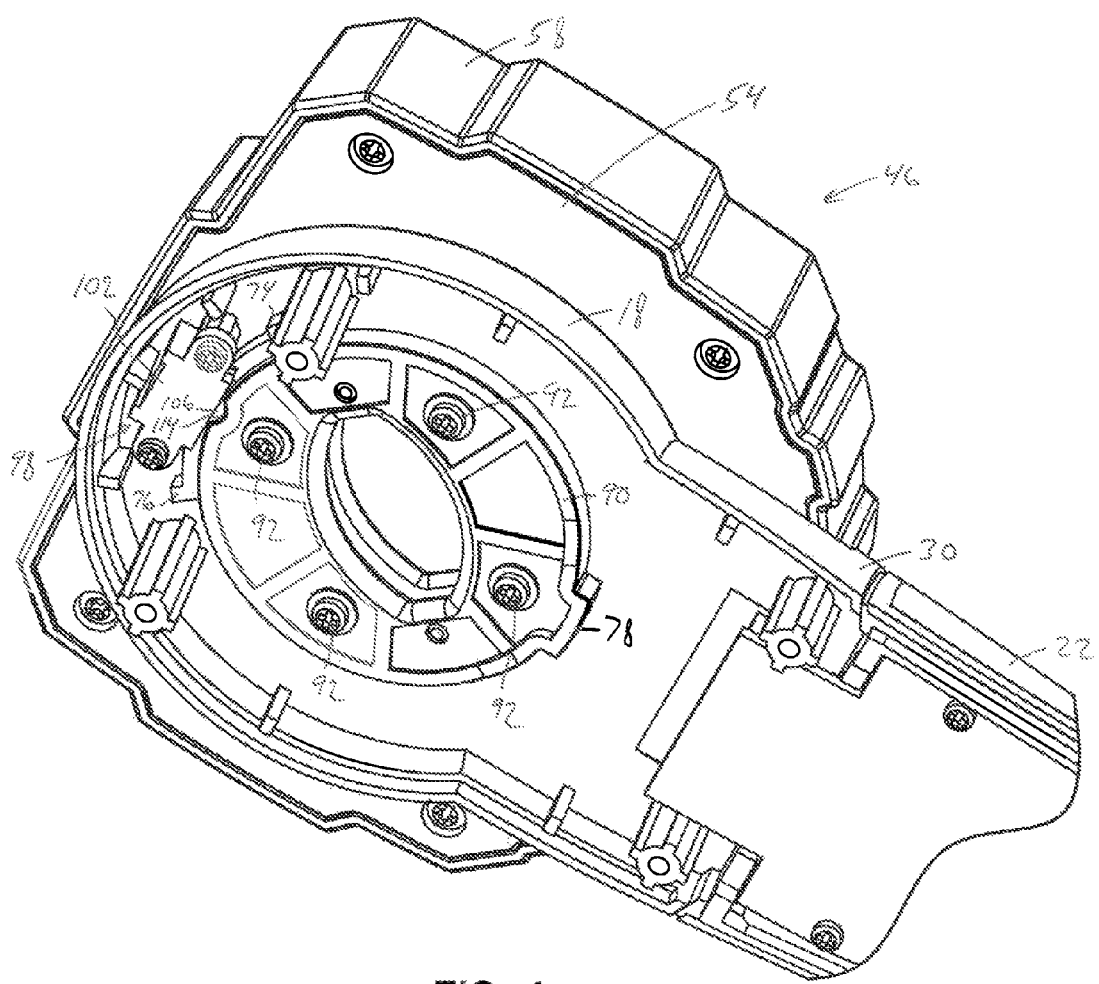
FIG. 4 is a partially assembled, rear perspective view of the visual inspection device of FIG. 1.

With reference to FIG. 3, the device 10 also includes a detent assembly 98 coupled to the upper shell 30 of the housing 14. The detent assembly 98 includes a housing 102 fastened to the upper shell 30 and positioned between the protrusions 74, 76, a detent 106 at least partially received within the housing 102, and a resilient member (e.g., a compression spring 110) biasing the detent 106 outwardly of the housing 102. The detent 106 is receivable within a recess 114 in the plate 90 to define a "home" or a default angular position of the display 46 relative to the housing 14 in which an image on the screen 50 is generally aligned with the longitudinal axis of the grip portion 22 of the housing 14 (see also FIGS. 4-6). In the illustrated construction of the device 10, the protrusion 78 is located about 180 degrees about the axis 66 from the recess 114. As such, one must rotate the display 46 substantially an equal amount from the home or default angular position of the display 46 to reach the first and second angular positions of the display 46, respectively.

During operation of the device 10, the user may have to manipulate the grip portion 22 of the housing 14 to position the camera assembly 44 in a particular manner relative to an object being viewed. Should the desired position of the camera assembly 44 require the grip portion 22 to be oriented non-parallel with a gravity vector passing through the user and/or the device 10, the display 46 may be pivoted or rotated relative to the housing 14 to orient the screen 50 with the gravity vector so that the user need not reposition their head to align themselves with the image on the screen 50.

Various features of the invention are set forth in the following claims.

What is claimed is:

1. A visual inspection device comprising:
   a housing including a support portion and a grip portion extending from the support portion;
   a flexible cable including a first end coupled to the housing and a second end;
   a camera assembly coupled to the second end of the flexible cable and operable to transmit image data through the flexible cable;
   a display movably coupled to the support portion of the housing and operable to present an image derived from the image data;
   wherein the housing includes a first protrusion, and wherein the display includes a second protrusion that is selectively engageable with the first protrusion to limit the movement of the display relative to the housing;
   wherein the housing includes a first shell and a second shell interconnected with the first shell, wherein the first end of the flexible cable is attached to the first shell, and wherein the first protrusion is integrally formed as a single piece with the second shell; and
   a plate coupled to the display for co-rotation with the display, wherein the second protrusion is configured as a radially outwardly extending tab on the plate; and wherein at least a portion of the second shell is clamped between the plate and the display to secure the display to the housing.

2. The visual inspection device of claim 1,
   wherein the first protrusion and the second protrusion are engaged to each other to define a first angular position of the display relative to the housing, and wherein the first protrusion and the second protrusion are disengaged from each other to define a second angular position of the display relative to the housing.

3. The visual inspection device of claim 2, wherein the display is rotatably coupled to the support portion of the housing.

4. The visual inspection device of claim 3, wherein the housing defines a first axis substantially aligned with the grip portion, and wherein the display is rotatable about a second axis oriented substantially normal to the first axis.

5. The visual inspection device of claim 4, wherein the first end of the flexible cable is substantially aligned with the second axis.

6. The visual inspection device of claim 1, wherein the housing includes a third protrusion angularly spaced from the first protrusion, and wherein the second and third protrusions are engaged to define the second angular position of the display relative to the housing.

7. The visual inspection device of claim 6, wherein the display is rotatable about 270 degrees between the first and second angular positions of the display relative to the housing.

8. The visual inspection device of claim 1, wherein the display is movable relative to the support portion of the housing to orient the image with a gravity vector through the device irrespective of an orientation of the grip portion of the housing.

9. The visual inspection device of claim 1, further comprising a battery pack removably received within a cavity in the grip portion of the housing.

10. The visual inspection device of claim 1, wherein the display includes a screen and a bezel surrounding the screen, and wherein the bezel includes an overmold to facilitate grasping the display and to help protect the screen from impacts.

11. The visual inspection device of claim 1, further comprising
a detent coupled to one of the housing and the display, and
a recess defined in the other of the housing and the display in which the detent is selectively received to maintain the display in a third angular position relative to the housing.

12. The visual inspection device of claim 11, wherein the display is rotatably coupled to the support portion of the housing about an axis, wherein the housing includes a third protrusion angularly spaced from the first protrusion, wherein the display includes the second protrusion which, when engaged with the first protrusion, defines the first angular position of the display relative to the housing and which, when engaged with the third protrusion, defines the second angular position of the display relative to the housing.

13. The visual inspection device of claim 12, wherein the third angular position is between the second and first angular positions.

14. The visual inspection device of claim 12, further comprising a detent housing coupled to the support portion of the housing in which the detent is at least partially received, wherein the detent housing is positioned between the first and third protrusions.

15. The visual inspection device of claim 11, further comprising a resilient member biasing the detent toward the recess.

16. The visual inspection device of claim 1, wherein
the display includes a screen, wherein the display is rotatably coupled to the support portion of the housing about a rotational axis that intersects the screen and operable to present an image derived from the image data, and wherein the first end of the flexible cable is aligned with the rotational axis.

* * * * *